(12) United States Patent
Kale et al.

(10) Patent No.: US 9,881,707 B2
(45) Date of Patent: Jan. 30, 2018

(54) X-RAY SHIELDING MATERIAL AND METHOD OF PREPARATION THEREOF

(71) Applicants: CENTRE FOR MATERIALS FOR ELECTRONICS TECHNOLOGY (C-MET), Pune, Maharashtra (IN); SECRETARY, DEPARTMENT OF ELECTRONICS AND INFORMATION TECHNOLOGY (DEITY), New Delhi (IN)

(72) Inventors: Bharat B. Kale, Pune (IN); Milind V. Kulkarni, Pune (IN); Rajendra P. Panmand, Pune (IN); Ujjwala V. Kawade, Pune (IN); Sanjay K. Apte, Pune (IN); Sonali D. Naik, Pune (IN); Jalindar D. Ambekar, Pune (IN); Ravindra S. Sonawane, Pune (IN); Dinesh P. Amlanerkar, Pune (IN); Nilofer Shroff, New Delhi (IN); Sandip Chatterjee, New Delhi (IN)

(73) Assignee: CENTRE FOR MATERIALS FOR ELECTRONICS TECHNOLOGY (C-MET), New Delhi (IN)

( * ) Notice: Subject to any disclaimer, the term of this patent is extended or adjusted under 35 U.S.C. 154(b) by 247 days.

(21) Appl. No.: 14/653,171

(22) PCT Filed: Dec. 17, 2013

(86) PCT No.: PCT/IN2013/000775
§ 371 (c)(1),
(2) Date: Jun. 17, 2015

(87) PCT Pub. No.: WO2014/097316
PCT Pub. Date: Jun. 26, 2014

(65) Prior Publication Data
US 2015/0287485 A1    Oct. 8, 2015

(30) Foreign Application Priority Data

Dec. 18, 2012 (IN) .......................... 3551/MUM/2012

(51) Int. Cl.
| | | |
|---|---|---|
| G21F 1/00 | (2006.01) |
| D01F 9/08 | (2006.01) |
| C01G 29/00 | (2006.01) |
| A61Q 17/04 | (2006.01) |
| A61K 8/23 | (2006.01) |
| A61K 8/02 | (2006.01) |
| G21F 1/08 | (2006.01) |
| G21F 1/10 | (2006.01) |
| A61K 8/25 | (2006.01) |
| A61K 8/37 | (2006.01) |
| C04B 35/622 | (2006.01) |
| A61K 8/35 | (2006.01) |
| A61K 8/73 | (2006.01) |
| C04B 35/547 | (2006.01) |

(52) U.S. Cl.
CPC ................ *G21F 1/00* (2013.01); *A61K 8/027* (2013.01); *A61K 8/23* (2013.01); *A61K 8/35* (2013.01); *A61K 8/37* (2013.01); *A61K 8/731* (2013.01); *A61Q 17/04* (2013.01); *C01G 29/006* (2013.01); *C04B 35/547* (2013.01); *C04B 35/62272* (2013.01); *D01F 9/08* (2013.01); *G21F 1/08* (2013.01); *G21F 1/10* (2013.01); A61K 2800/413 (2013.01); C01P 2002/72 (2013.01); C01P 2004/16 (2013.01); C01P 2004/61 (2013.01); C01P 2004/64 (2013.01); C01P 2006/90 (2013.01); C04B 2235/3215 (2013.01); C04B 2235/3298 (2013.01); C04B 2235/526 (2013.01); C04B 2235/5264 (2013.01); C04B 2235/761 (2013.01); Y10T 428/298 (2015.01)

(58) Field of Classification Search
None
See application file for complete search history.

(56) References Cited

U.S. PATENT DOCUMENTS

| | | | |
|---|---|---|---|
| 4,670,658 A | 6/1987 | Meyers et al. | |
| 6,459,091 B1 | 10/2002 | DeMeo et al. | |
| 2006/0204738 A1* | 9/2006 | Dubrow .................. | A61F 13/02 428/292.1 |
| 2010/0044599 A1 | 2/2010 | McCord | |

FOREIGN PATENT DOCUMENTS

| | | | |
|---|---|---|---|
| CN | 101391813 A | * | 3/2009 |
| CN | 101613882 B | * | 12/2011 |
| CN | 102672162 | | 9/2012 |

OTHER PUBLICATIONS

Singh, S., et al., "Synthesis and characterization of bismuth doped barium sulphide nanoparticles", Materials Research Bulletin, 2010, pp. 523-526.*
CN101391813A translation, "Preparation of Monodisperse Bismuth Sulfide Nanoparticles by Template Method", accessed from: https://encrypted.google.com/patents/CN101391813A?cl=zh; accessed on Sep. 27, 2017, pp. 1-6.*

(Continued)

*Primary Examiner* — Michael G Hartley
*Assistant Examiner* — Lance Rider
(74) *Attorney, Agent, or Firm* — Ladas & Parry LLP

(57) ABSTRACT

The present disclosure relates to a process for synthesis of barium bismuth sulfide nanofibers, having equivalent shielding capacity as lead. The present disclosure also relates to a radiation shielding articles and cosmeceuticals.

5 Claims, 2 Drawing Sheets

(56) References Cited

OTHER PUBLICATIONS

Figure 1:
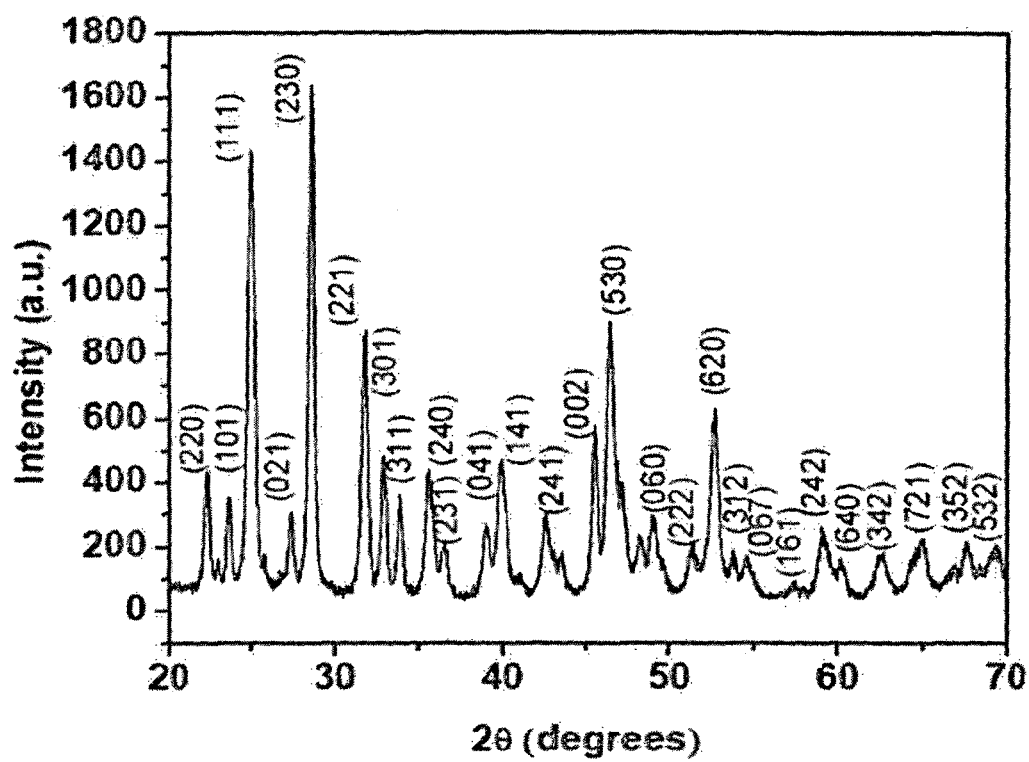

CN101613882B translation, "Method for preparing bismuth sulfide nanorod crystal material", accessed from: https://encrypted.google.com/patents/CN101613882B?cl=zh, accessed on: Sep. 27, 2017, pp. 1-5.*
Hopwood, J.D., et al., "Synthesis of Barium Sulfate Nanoparticles and Nanofilaments in Reverse Micelles and Microemulsions", Chem. Mater., 1997, pp. 1819-1828.*
English Translation of CN 102672162.
Surender Singh, et al.: 'Synthesis and Characterization of Bismuth Doped Barium Sulphide Nanoparticles' Materials Research Bulletin, vol. 45, No. Issue, May 2010, pp. 523-526.
Cherdsak Bootjomchai, et al.: 'Gamma-Ray Shielding and Structural Properties of Barium-Bismuth-Borosilicate Glasses' Radiation Physics and Chemistry, vol. 81, No. Issue, Jul. 2012, pp. 785-790.

* cited by examiner

X-RAY SHIELDING MATERIAL AND METHOD OF PREPARATION THEREOF

RELATED APPLICATION INFORMATION

This application is a 371 of International Application PCT/IN2013/000775 filed 17 Dec. 2013, which claims priority from India Application No.: 3551/MUM/2012 filed 18 Dec. 2012, the content of which is incorporated herein by reference.

FIELD OF THE DISCLOSURE

The present disclosure relates to an X-ray shielding material and a process for synthesis thereof. The present disclosure also relates to radiation shielding articles and radiation shielding cosmeceuticals.

BACKGROUND

Modern diagnostic radiology assures faster, more precise diagnosis and enables monitoring of a large proportion of diseases by using of ionising radiations such as X-rays, gamma rays, beta rays and electrons. The inherent properties of these ionising radiations provide many diagnostic benefits but also prone to cause the potential health problems. It is well established that the effects of these radiation are cumulative and lead to increased incidence of cancers, cell deaths and genetic damages. Therefore, protection against ionising radiation has achieved central importance to avoid health related problems in patients and in radiation laboratory technicians.

In order to ensure minimal X-ray radiation penetration, individuals who come in contact with X-rays are required to wear lead-lined protection wear, such as aprons, gloves, goggles, and thyroid protection. Three different categories of wearable protection include total (100%) lead-lined clothing, lead composite clothing, and non-lead clothing. While the total lead lined clothing has the highest protection against high and scattered low energy radiation, it is inflexible, extremely heavy (15.1 lbs/sq yard) and can cause severe neck and back problems for individuals who wear them for many hours. Furthermore, lead has been recognized as major environmental pollutant, including the lead used for radiation shielding in radiotherapy.

Therefore, in accordance with the present disclosure there is envisaged a nontoxic material having equivalent radiation shielding capability as lead.
Objects:
Some of the objects of the present disclosure, which at least one embodiment herein satisfies, are as follows:

It is an object of the present disclosure to ameliorate one or more problems of the prior art or to at least provide a useful alternative.

It is another of the present disclosure to provide bimetallic nanofibers which can be used as a substitute for lead in X-ray shielding application.

It is yet another object of the present disclosure to provide a process for synthesis of bimetallic nanofibers.

It is still another object of the present disclosure to provide an X-ray shielding article.

It is a further object of the present disclosure to provide an X-ray shielding composition having medicinal and/or cosmetic applications.

In accordance with one aspect of the present disclosure there is provided a process for synthesis of barium bismuth sulfide nanofibers, said process comprising the following steps;

a. dissolving barium nitrate, bismuth nitrate pentahydrate and thiourea in a solvent system to obtain a dispersion containing complex of barium bismuth sulfide; and
b. mixing at least one surfactant in the dispersion under continuous agitation to obtain a homogeneous mixture;
c. heating the homogeneous mixture at a temperature ranging between 120° C. and 180° C. in an apparatus for 24 hours followed by cooling at a temperature ranging between 20° C. and 30° C. to obtain a precipitate; and
d. washing the precipitate by employing at least one solvent selected from the group consisting of water, ethanol, methanol, isopropanol and acetone to obtain nanofibers of barium bismuth sulfide.

Typically, the solvent system is a combination of ethylene glycol and water at a proportion ranging between 1:1 and 3:1.

Typically, the surfactant is at least one selected from the group consisting of cetyl trimethylammonium bromide, polyvinyl alcohol and polyethylene glycol p-(1,1,3,3-tetramethylbutyl)-phenyl ether.

Typically, the average diameter of the nanofibers is between 20 nm and 50 nm.

Typically, the average length of the nanofibers is between of 1 μm and 3 μm.

Typically, Barium bismuth sulfide nanofibers are characterized by (a) diameter of 20 nm to 50 nm and (b) the length of 1 μm to 3 μm and the X-Ray diffraction pattern having 2θ values at 28.58, 24.95, 46.52, 31.82, 52.7, 45.53, 32.87, 39.89 and 35.48.

In accordance with another aspect of the present disclosure there is provided a coating composition comprising barium bismuth sulfide nanofibers in an amount ranging between 10% and 60%, preferably between 20% and 40% of the total mass of said composition, at least one thinner and at least one color guard.

Typically, the thinner is at least one selected, from the group consisting of ethyl methyl ketone, amyl acetate and acetone in an amount ranging 10% and 90%, preferably between 20% and 80% of the total mass of said composition.

Typically, the color guard is at least one selected from the group consisting of epoxy, nitrocellulose and ethyl cellulose in an amount ranging between 5% and 30%, preferably between 8% and 12%.

In accordance with another aspect of the present disclosure there is provided a process for preparation of a coating composition comprising barium bismuth sulfide nanofibers; said process comprising the following steps:

a. milling barium bismuth sulfide nanofibers to obtain a mass; and
b. adding at least one color guard and at least one thinner into the mass followed by mixing to obtain a coating composition.

Typically, milling is carried out for a time period ranging between 12 hours and 48 hours, preferably between 20 hours and 25 hours.

In accordance with another aspect of the present disclosure there is provided a process for the preparation of an X-ray shielding article; said process comprising the following steps:

a. contacting said article with coating composition comprising barium bismuth sulfide nanofibers, at least one thinner and at least one, color guard to obtain a coated article; and b. annealing the coated article by hot air at a temperature ranging between 50° C. and 60° C. for a time period ranging between 0.5 and 2 min. to obtain X-ray shielding article.

Typically, the amount of barium bismuth sulphide nanaofibers is in the range between 10% and 60%, preferably between 20% and 40% of the total mass of said composition.

Typically, the article is at least one selected from the group consisting of aprons, gowns, scrubs, uniforms, gloves, caps, masks, curtains, sheets, fabrics, shoe covers, drapes, surgical pads, protective screens, thyroid collars, thyroid shields, desks, drawers, rooms, walls, partitions, panels, tables, chairs and cabinets.

Typically, the article is contacted with coating composition by at least one method selected from the group comprising applying, spraying, dipping, incorporating brushing and painting. Typically, the color guard is at least one selected from the group consisting of epoxy, nitrocellulose and ethyl cellulose in an amount ranging between 5% and 30%, preferably between 8% and 12% of the total mass of said composition.

Typically, the thinner is at least one selected from the group consisting of Ethyl methyl ketone, amyl acetate and acetone in an amount ranging 10% and 90%, preferably between 20% and 80% of the total mass of said composition.

In accordance with another aspect of the present disclosure there is provided an X-ray shielding composition comprising barium bismuth sulfide nanofibers, in the range of 20% and 30% of the total mass of the said composition and at least one pharmaceutically acceptable excipient.

Typically, the excipient is at least one selected from the group consisting of gelling agent, emulsifiers, surfactants, humectants, preservatives, antioxidants, opacifiers, colorants, propellants, gelling agents, waxes and oils.

Typically, said X-ray shielding composition is in a form selected from the group consisting of gels, creams, lotions, sprays and ointments.

BRIEF DESCRIPTION OF ACCOMPANYING DRAWINGS

FIG. 1: Illustrates X-Ray Diffraction (XRD) pattern of barium bismuth sulfide nanofibers; and FIG. 2: Illustrates Field—Emission Scanning Electron Microscopy analysis of barium bismuth sulfide nanofibers.

DETAILED DESCRIPTION

Present disclosure is particularly directed to solve the aforementioned problems associated with the use of lead or lead alloy as an X ray shielding material. This is accomplished by preparing a lead free X-Ray shielding material such as nanofibers of barium bismuth sulfide. In accordance with first aspect of the present disclosure there is provided a process for hydrothermal synthesis of barium bismuth sulfide nanofibers.

In the first step, barium nitrate, bismuth nitrate pentahydrate and thiourea is dissolved in a solvent system which contains ethylene glycol and water to obtain a dispersion containing barium bismuth sulfide complex. In accordance with the present disclosure the proportion of ethylene glycol to water is maintained between 1:1 and 3:1.

In the second step, at least one surfactant is mixed with the dispersion under continuous agitation for an hour to obtain a mixture. Further the mixture is heated at a temperature ranging between 120° C. and 180° C. in an apparatus for 24 hours which is then cooled at a temperature ranging between 20° C. and 30° C. to obtain a precipitate containing nanofibers of barium bismuth sulfide. The precipitate is washed several times with water and ethanol to obtain crystals of nanofibers of barium bismuth sulfide. The ethylene glycol used in said process influences the formation of urchin flower like morphology of the nanofibers of barium bismuth sulfide. The surfactants or capping agents are selected from the group such as cetyl trimethylammonium bromide, polyvinyl alcohol and polyethylene glycol p-(1,1,3,3-tetramethylbutyl)-phenyl ether. The surfactants reduces the surface tension of ethylene glycol and lowers the energy needed to form a new phase which in turn facilitates production of nanofibers of barium bismuth sulfide at a lower super saturation. Furthermore, in the crystallization process of nanofibers of barium bismuth sulfide, surfactant molecules serves as a growth controller as well as an agglomeration inhibitor by forming a covering film on the newly formed barium bismuth sulfide nanofibers.

Barium bismuth sulfide nanofibers obtained in said process has diameter ranging between 20 nm and 50 nm and length ranging between of 1 µm and 3 µm and the X-Ray diffraction pattern having 2θ values at 28.58, 24.95, 46.52, 31.82, 52.7, 45.53, 32.87, 39.89 and 35.48

In accordance with another aspect of the present disclosure there is provided a coating composition containing barium bismuth sulfide nanofibers in the range of 10% to 60% with respect to the total mass of said composition along with at least one thinner and at least one color guard.

In accordance with another aspect of the present disclosure there is provided a process for preparation of a coating composition containing barium bismuth sulfide nanofibers, at least one thinner and at least one color guard. The method involves the following steps;

In the first step, barium bismuth sulfide nanofibers are milled for a time period ranging between 12 hours and 48 hours. Barium bismuth sulfide nanofibers is used in the range of 10% to 60% with respect to the total mass of said composition to obtain a mass.

In second step, said mass is admixed with at least one color guard and at least one thinner to obtain the coating composition.

The thinner used in the present disclosure includes but is not limited to ethyl methyl ketone, amyl acetate and acetone in an amount ranging between 10% and 90% of the total mass of said composition.

The color guard used in the present disclosure includes but is not limited light aliphatic Solvent naphtha, n-hexane, xylene, acetone, ethyl benzene, amorphous silica, fumed and crystalline free carbon black, epoxy, nitrocellulose and ethyl cellulose and in an amount ranging between 5% and 30% of the total mass of said composition.

In accordance with another aspect of the present disclosure there is provided a process for the preparation of a X-ray shielding article; the process is described herein below The article is contacted with said coating composition of the present disclosure by using at least one method selected from the group consisting of applying, spraying, dipping, incorporating and brushing to obtain a coated article and then annealed by hot air at a temperature ranging between 50° C. and 60° C. for a time period ranging between 0.5 and 2 min. obtain an X-Ray shielding article.

In accordance with one of the embodiment of the present disclosure the coating composition of the present disclosure is applied as paint on desks, drawers, rooms, walls, partitions, panels, tables, chairs and cabinets.

The article having X-ray shielding property includes but is not limited to aprons, gowns, scrubs, uniforms, gloves, caps, masks, curtains, sheets, fabrics, shoe covers, drapes, surgical pads, protective screens, thyroid collars, thyroid shields, desks, drawers, rooms, walls, partitions, panels, tables, chairs and cabinets.

In accordance with another aspect of the present disclosure there is provided an X ray shielding composition, which is prepared by using barium bismuth sulfide nanofibers and at least one pharmaceutically acceptable excipient.

The excipient used for preparation of said X ray shielding composition includes but are not limited to gelling agent, emulsifiers, surfactants, humectants, preservatives, antioxidants, opacifiers, colorants, propellants, gelling agents, waxes, and oils the like.

The X ray shielding composition of the present disclosure can be prepared in the any one of the listed forms such as gels, creams, lotions, sprays, and ointments and the like.

EXAMPLE 1

Synthesis of Barium Bismuth Sulfide 0.9701 gm of Bismuth Nitrate Pentahydrate (Bi(NO)$_3$·5H$_2$O), 0.6089 gm of thiourea (SC(NH$_2$)$_2$) and 0.2613 gm of Barium Nitrate (Ba(NO$_3$)$_2$) was dissolved in 80 ml of solvent system containing Ethylene Glycol : Water (3:1) to obtain a dispersion of barium bismuth sulfide. Subsequently 500 ppm of polyethylene glycol p-(1,1,3,3-tetramethylbutyl)-phenyl ether and cetyl trimethylammonium bromide was added into the dispersion under continuous stirring for an hour to obtain a mixture. The mixture was heated at a temperature of 150° C. in an autoclave for 24 hours and then cooled at a temperature of 25° C. to obtain a precipitate. The precipitate obtained was then separated by filtration and further crystalized with water and ethanol to obtain barium bismuth sulfide nanofibers.

EXAMPLE 2

Preparing Coating Composition 25 gm of barium bismuth sulfide was milled in a ball mill for 24 hours to obtain barium bismuth sulfide in the form of powder. Mixing 12 gm of color guard and 100 ml of ethyl ketone (thinner) in to 25 gm of barium bismuth sulfide powder to obtain coating composition.

EXAMPLE 3

Preparing X-ray Shielding Article 100 ml of coating composition was coated on an article by dip coating method. This coating was then annealed at a temperature of 55° C. to insure barium bismuth sulfide particle adhesion on the surface of the article.

Characterization:

The X-ray shielding property of barium bismuth sulfide coated article (X-ray shielding article) was tested using the X-ray source and the Leakage radiation meter. The X-ray penetration with respect to thickness of the material is also tested. The X-ray source (60 Kv and 80 Kv) was obtained from Bharat Electronics (BEL) Pune; whereas the Leakage Radiation Meter, that formed a part of the testing machine, was obtained from PTW, Germany. The numerical readings show the linearity in the absorption. The thickness dependent study with 60 Kv and 80 Kv of the apron has been performed. The results were summarized in the Table 1.

TABLE 1

X-ray absorption of X-ray shielding article at 60 Kv potential 48.6 smAS voltage.

| No | Measurement's | Thickness of the X-ray shielding article (μm) | X-ray Transmitted (μ Gray) | X-ray absorbance (μ Gray) | X-ray absorbance (%) |
|----|---------------|-----------------------------------------------|----------------------------|---------------------------|----------------------|
| 1 | Direct exposed | 240 | 1022 | — | — |
| 2 | Single | 240 | 234.5 | 787.5 | 77.054 |
| 3 | Two fold | 480 | 81.7 | 940.3 | 92.005 |
| 4 | Four fold | 960 | 13.4 | 1008.6 | 98.68 |

TABLE 2

X-ray absorption of X-ray shielding article at 80 Kv potential 64.4 smAS voltage.

| No | Measurement's | Thickness of the X-ray shielding article (μm) | X-ray Transmitted (μ Gray) | X-ray absorbance (μ Gray) | X-ray absorbance (%) |
|----|---------------|-----------------------------------------------|----------------------------|---------------------------|----------------------|
| 1 | Direct exposed | 240 | 1903 | — | — |
| 2 | Single | 240 | 649.7 | 1253.3 | 65.85 |
| 3 | Two fold | 480 | 298.0 | 1605 | 84.34 |
| 4 | Four fold | 960 | 90.7 | 1812.3 | 95.23 |

From the above results it is concluded that the X-ray absorption increases with thickness and found to be saturated to 960 μm.

X-Ray Diffraction (XRD):

The XRD pattern of nanofibers of barium bismuth sulfide is shown in FIG. 1. The XRD peaks are found to be sharp and distinct, which indicate the crystalline nature of the compound. The indexing of the compound has been carried out with the help of X'pert high score plus software. The obtained pattern is matched with the standard JCPDS card no. 76-1459 and found to have hexagonal structure. The unit cell parameters of the compound are found to be a=21.77, b=21.77 and c=4.153 Å. (FIG. 1)

Figure 2:
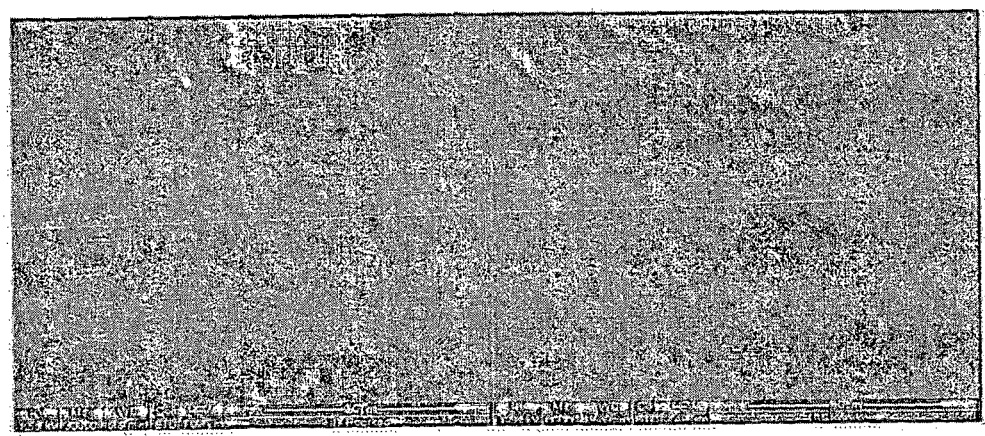

Field-Emission Scanning Electron Microscopy Analysis (FESEM):

Morphological study of barium bismuth sulfide (BaBi$_2$S$_4$) nanofibers was performed by FESEM and recorded on JOEL instrument (IIT Roorkee). The images obtained from FESEM demonstrated fiber-like morphology. The particle size of barium bismuth sulfide (BaBi$_2$S$_4$) nanofibers was found to be ranging between 20-50 nm and its length was found to be 1-3 μm. (FIG. 2)

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

"Whenever a range of values is specified, a value up to 10% below and above the lowest and highest numerical value respectively, of the specified range, is included in the scope of the invention".

While considerable emphasis has been placed herein on the particular features of this invention, it will be appreciated that various modifications can be made, and that many changes can be made in the preferred embodiments without departing from the principle of the invention. These and other modifications in the nature of the invention or the preferred embodiments will be apparent to those skilled in the art from the disclosure herein, whereby it is to be distinctly understood that the foregoing descriptive matter is to be interpreted merely as illustrative of the invention and not as a limitation.

The invention claimed is:

1. A process for synthesis of barium bismuth sulfide nanofibers, said process comprising the following steps;
    a. dissolving barium nitrate, bismuth nitrate pentahydrate and thiourea in a solvent system to obtain a dispersion containing complex of barium bismuth sulfide; and
    b. mixing at least one surfactant in the dispersion under continuous agitation to obtain a mixture;
    c. heating the mixture at a temperature ranging between 120° C. and 180° C. in an apparatus for 24 hours followed by cooling at a temperature ranging between 20° C. and 30° C. to obtain a precipitate; and
    d. washing the precipitate by employing at least one solvent selected from the group consisting of water, ethanol, methanol, isopropanol, and acetone to obtain nanofibers of barium bismuth sulfide.

2. The process as claimed in claim 1, wherein the solvent system is a combination of ethylene glycol and water at a proportion ranging between 1:1 and 3:1.

3. The process as claimed in claim 1, wherein the surfactant is at least one selected from the group consisting of cetyl trimethylammonium bromide, polyvinyl alcohol and polyethylene glycol p-(1,1,3,3-tetramethylbutyl)-phenyl ether.

4. The process as claimed in claim 1, wherein the average diameter of the nanofibers is between 20 nm and 50 nm.

5. The process as claimed in claim 1, wherein the average length of the nanofibers is between of 1 μm and 3 μm.

* * * * *